(12) United States Patent
Bucciaglia et al.

(10) Patent No.: US 11,039,849 B2
(45) Date of Patent: Jun. 22, 2021

(54) ANTI-BUCKLING ACTUATOR

(71) Applicant: JustRight Surgical, LLC, Louisville, CO (US)

(72) Inventors: Joseph D. Bucciaglia, Boulder, CO (US); Richard N. Granger, Niwot, CO (US); Allison B. Lyle, Boulder, CO (US); Ruth Beeby, Santa Clara, CA (US); Jerome Adam-Cote, Mountain View, CA (US)

(73) Assignee: Bolder Surgical, LLC, Louisville, CO (US)

( * ) Notice: Subject to any disclaimer, the term of this patent is extended or adjusted under 35 U.S.C. 154(b) by 320 days.

(21) Appl. No.: 16/017,857

(22) Filed: Jun. 25, 2018

(65) Prior Publication Data

US 2018/0368867 A1 Dec. 27, 2018

Related U.S. Application Data

(60) Provisional application No. 62/524,727, filed on Jun. 26, 2017.

(51) Int. Cl.
*A61B 17/072* (2006.01)
*A61B 17/28* (2006.01)
(Continued)

(52) U.S. Cl.
CPC .......... *A61B 17/282* (2013.01); *A61B 17/068* (2013.01); *A61B 17/07207* (2013.01);
(Continued)

(58) Field of Classification Search
CPC .. A61B 2017/2937; A61B 2017/07285; A61B 2017/00345; A61B 2090/034;
(Continued)

(56) References Cited

U.S. PATENT DOCUMENTS 10,143,474 B2 12/2018 Bucciaglia et al.
2009/0206140 A1\* 8/2009 Scheib .............. A61B 17/07207
227/176.1
(Continued)

FOREIGN PATENT DOCUMENTS

WO 2019/005705 1/2019

OTHER PUBLICATIONS

Young, Lee W. "International Search Report and Written Opinion for PCT/US2018/039371," dated Aug. 30, 2018, 6 pages, published in: CH.

(Continued)

*Primary Examiner* — Chelsea E Stinson
*Assistant Examiner* — Himchan Song
(74) *Attorney, Agent, or Firm* — Schneider IP Law LLC; Laura A. Schneider

(57) ABSTRACT

A clamping mechanism for a surgical instrument and related methods are disclosed. Upper and lower elongated members are configured to engage each other at a first interlock and a second interlock, the first interlock distal of the second interlock. The clamping mechanism is movable between a first configuration, a second configuration, and a third configuration. In the first configuration, the elongated members are approximated towards each other and the first and second interlocks are not engaged. In the second configuration, the distal portion of the elongated members are moved away from each other, the first interlock is engaged, and the second interlock is not engaged. In the third configuration, the distal portions of the elongated members are moved away from each other relatively, the proximal portions of the elongated members are moved away from each other relatively, the first interlock is engaged, and the second interlock is engaged.

21 Claims, 23 Drawing Sheets

(51) Int. Cl.
*A61B 17/285* (2006.01)
*A61B 18/14* (2006.01)
*A61B 17/068* (2006.01)
*A61B 90/00* (2016.01)
*A61B 17/29* (2006.01)
*A61B 17/00* (2006.01)

(52) U.S. Cl.
CPC ........ *A61B 17/285* (2013.01); *A61B 18/1442* (2013.01); *A61B 2017/00345* (2013.01); *A61B 2017/07285* (2013.01); *A61B 2017/2937* (2013.01); *A61B 2090/034* (2016.02)

(58) Field of Classification Search
CPC .............. A61B 18/1442; A61B 17/285; A61B 17/07207; A61B 17/068; A61B 17/282
USPC ............................................ 227/175.1–182.1
See application file for complete search history.

(56) References Cited

U.S. PATENT DOCUMENTS

| | | |
|---|---|---|
| 2013/0008937 A1 | 1/2013 | Viola |
| 2013/0098969 A1 | 4/2013 | Scirica et al. |
| 2013/0119109 A1* | 5/2013 | Farascioni ........... A61B 17/068 227/175.1 |
| 2015/0173746 A1* | 6/2015 | Baxter, III ....... A61B 17/07207 227/180.1 |
| 2016/0345971 A1* | 12/2016 | Bucciaglia ....... A61B 17/07207 |
| 2017/0007236 A1 | 1/2017 | Shelton, IV et al. |
| 2017/0095251 A1 | 4/2017 | Thompson et al. |
| 2017/0231633 A1 | 8/2017 | Marczyk et al. |
| 2017/0284372 A1 | 10/2017 | Teichert |
| 2018/0070945 A1 | 3/2018 | Racenet et al. |
| 2018/0125485 A1 | 5/2018 | Beardsley et al. |
| 2018/0250006 A1 | 9/2018 | Bucciaglia et al. |

OTHER PUBLICATIONS

Gillespie, Richard, Response and amended claims filed in EP Application No. 18825383.5, dated Jul. 17, 2020, Published in: EP, 8 pages.

* cited by examiner

ANTI-BUCKLING ACTUATOR

CROSS-REFERENCE TO RELATED APPLICATIONS

This application claims priority to U.S. Provisional Application No. 62/524,727, filed Jun. 26, 2017 and entitled "Anti-buckling Actuator," the entire disclosure of which is hereby incorporated by reference for all proper purposes.

FIELD OF THE INVENTION

The present invention relates generally to surgical instruments, and more specifically to actuators and/or clamping mechanisms for surgical instruments.

BACKGROUND OF THE INVENTION

There is a need for an actuator for a surgical instrument that is robust particularly for small instruments, such as, for example, surgical sealing and cutting instruments of around 5 millimeters in diameter or less.

As surgical instruments become smaller to provide a less invasive surgical option for infants and/or weakened or elderly patients, it is becoming necessary to provide material and mechanical solutions that overcome the constraints of material physics. More to the point, one cannot simply "shrink" larger surgical instruments to achieve a functioning small or micro-sized instrument, because the materials cannot withstand the focused forces that are expected at the small or micro size.

In some cases, it is desirable to apply a clamping and/or cutting force to a surgical stapler or sealer that is very small or micro-sized.

SUMMARY OF THE INVENTION

Embodiments disclosed herein address the above stated need.

BRIEF DESCRIPTION ON THE DRAWINGS

DETAILED DESCRIPTION

Figure 1:
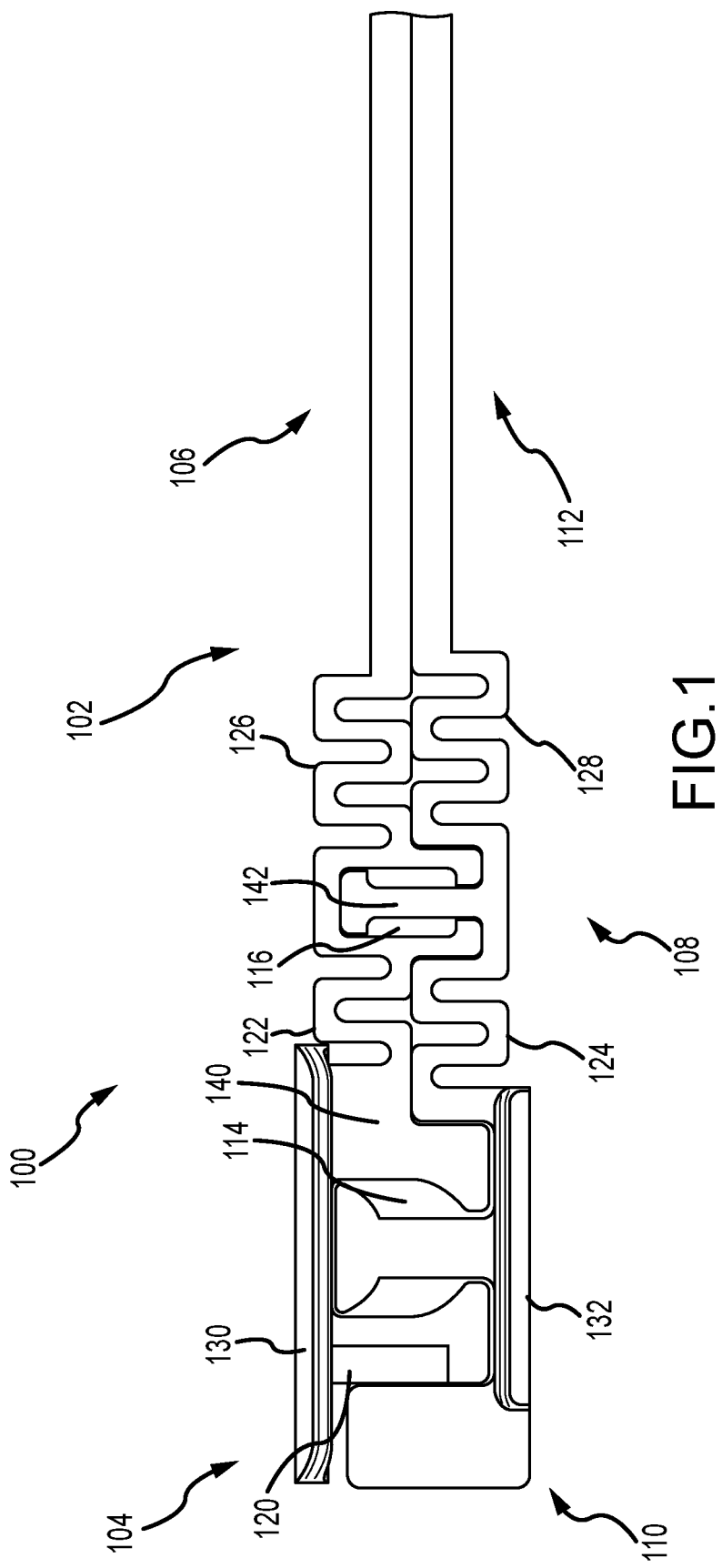
FIG. 1 is a side view of an expanding actuator having a second lock.

The word "exemplary" is used herein to mean "serving as an example, instance, or illustration." Any embodiment described herein as "exemplary" is not necessarily to be construed as preferred or advantageous over other embodiments. The words "upper" and "lower" may be referenced herein as "first" and "second", and, of course, may be reversed by reversing orientation. All terms used to indicate absolute values or positions should be understood to mean values within a reasonable manufacturing tolerance at the time of manufacture or as of this writing, whichever is greater.

Referring to FIGS. 1-32, in some embodiments, a surgical stapler or sealer may be provided with a cutting mechanism 120 that is pushed distally to sever tissue clamped between a pair of jaws or anvil/cartridge housing. Those skilled in the art will recognize that, to operate the cutting mechanism 120 in this manner, solutions known to larger instruments will not provide the necessary rigidity and strength needed to sever the tissue. Other solutions are necessary.

The inventors have provided, and it is described herein, a clamping mechanism 100 with a cutting mechanism 120 that is pushed distally by an actuator positioned at a proximal portion of the instrument. As the clamping mechanism 100 travels distally, portions of the clamping mechanism 100, such as an upper I-beam portion 130 and a lower I-beam portion 132, are configured to expand to travel external to the jaws/anvil/cartridge housing (see FIG. 31). Portions of the clamping mechanism 100 are shaped and configured with a rigidized section 140, 142 and a flex portion(s) 122, 124, 126, 128 to provide an optimized balance between flexibility and rigidity in the clamping mechanism 100. The rigidized section(s) 140, 142 may be a portion of an elongated member 102, 108 that is thickened so as to reduce the ability of the material to bend. The flex portion(s) 122, 124, 126, 128 may be areas in which the elongated member(s) 102, 108 are cut out, thinned, tapered, etc., to allow the material to bend.

Figure 2:
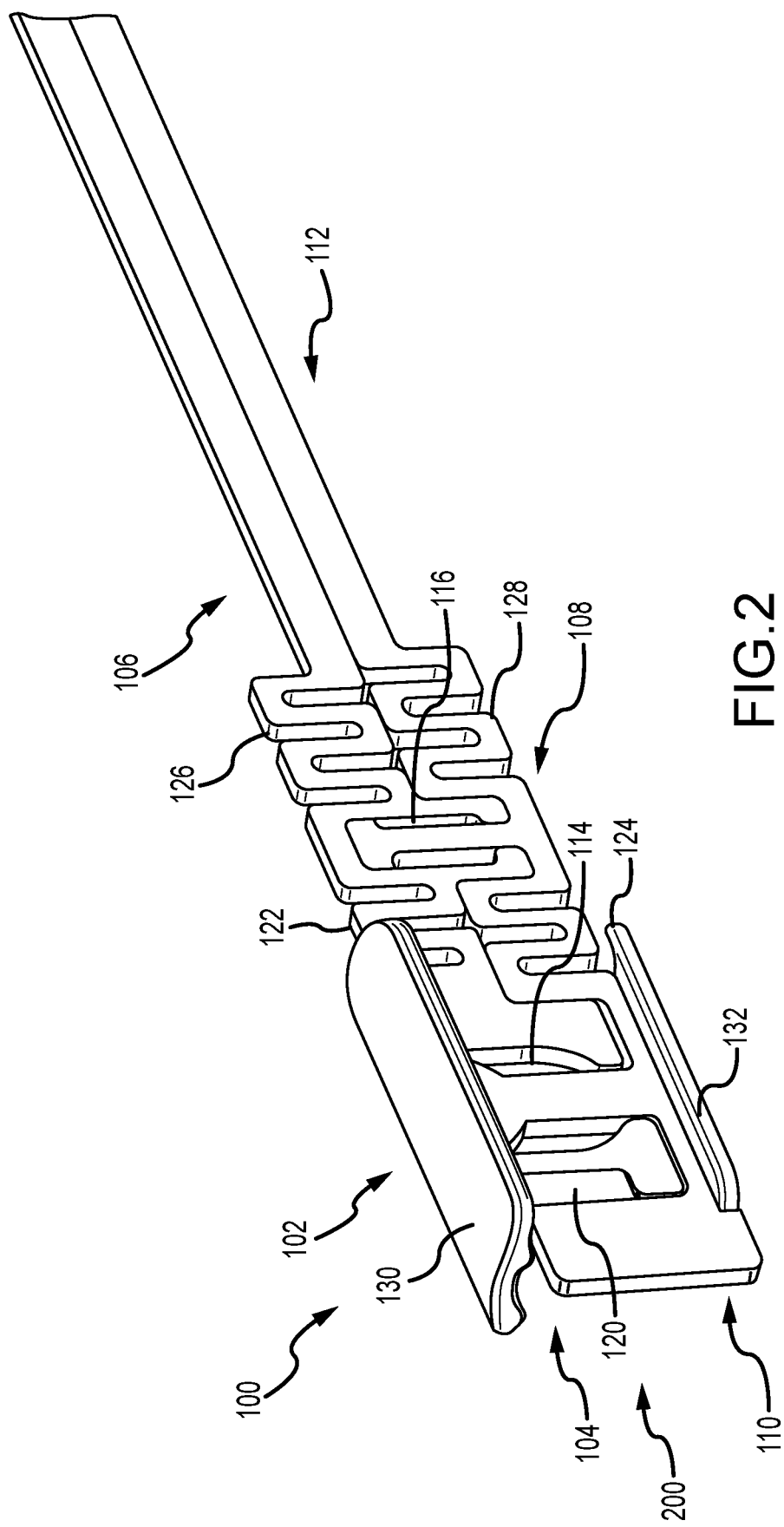
FIG. 2 is a perspective view of the actuator in FIG. 1.
Figure 3:
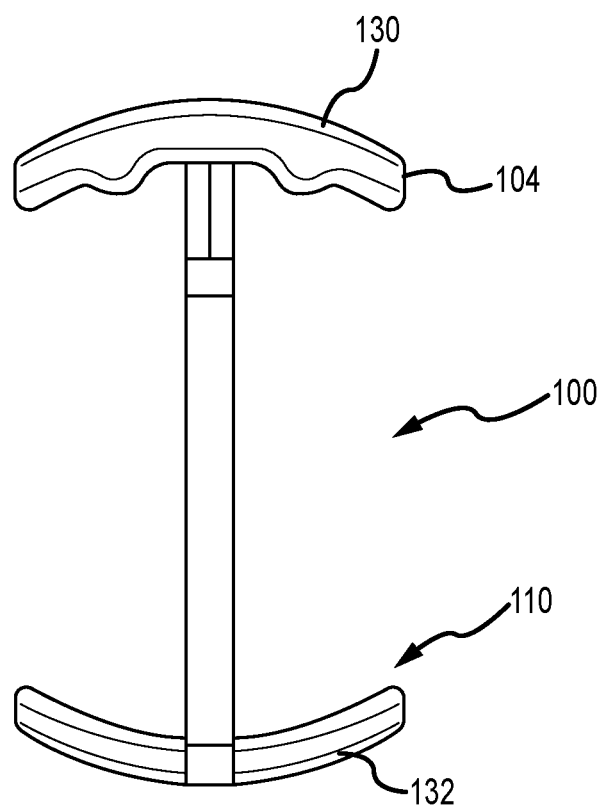
FIG. 3 is an end view of the actuator in FIG. 1.
Figure 26:
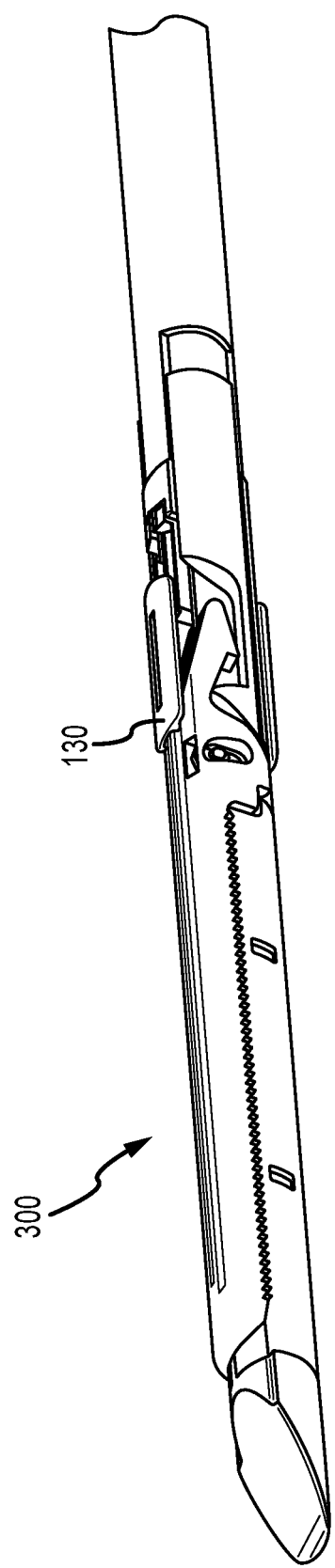
FIG. 26 is a perspective view of a surgical stapler with the mechanism in FIG. 23.
Figure 27:
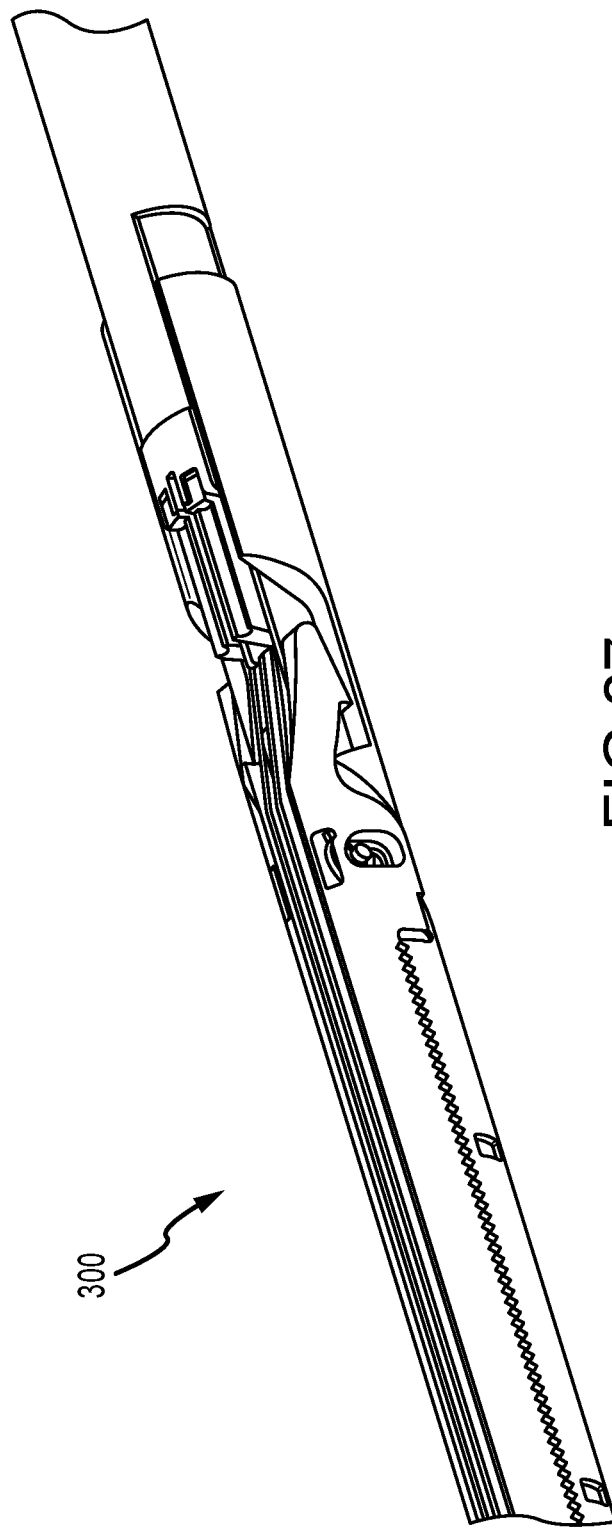
FIG. 27 is a perspective view of alignment features of the surgical stapler in FIG. 26.

Referring to FIGS. 1-3, a clamping mechanism 100 as described herein may operate or be configured to operate with a surgical instrument 300 (see e.g. FIGS. 26-27) that is similar to the surgical instrument 300 or cutting mechanism described in co-pending U.S. patent application Ser. No. 15/148,744, published on Dec. 1, 2016 as US 2016/0345971 A1, entitled Surgical Stapler, to Bucciaglia et al., the entire contents of which are incorporated herein by reference for all proper purposes. The actuator 100, which may be interchangeably referenced herein as a clamping mechanism 100, may be dynamic, so as to effectively operate an expanding I-beam 200. Flexible portions 122, 124, 126, 128 allow the upper elongated member 102 and/or lower elongated member 104 to diverge during the approach to full extension (see FIG. 26 illustrating the expansion of the I-beam portions 130, 132 and FIG. 27 illustrating the alignment features). In some embodiments, buckling may be controlled by adding an additional height restriction. With buckling controlled, axial force transmission may improve.

At full extension the clamp load may encourage the primary lock feature on the upper actuator to open, allowing the tab on the lower actuator to escape. This load may then be distributed in part to the secondary locking feature, preventing separation of the upper and lower actuator. The chamfers may allow the upper and/or lower actuators to tilt during the approach to full extension.

Figure 4:
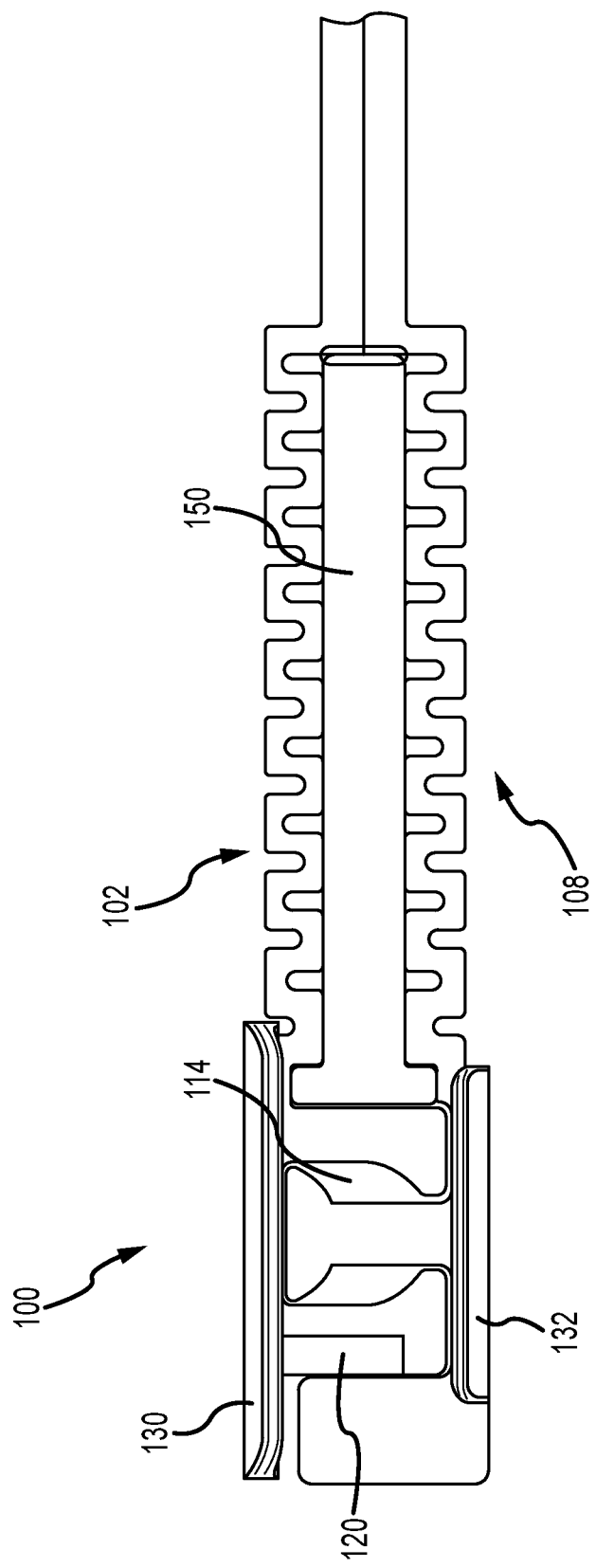
FIG. 4 is a side view of an expanding actuator with a rigid push.
Figure 5:
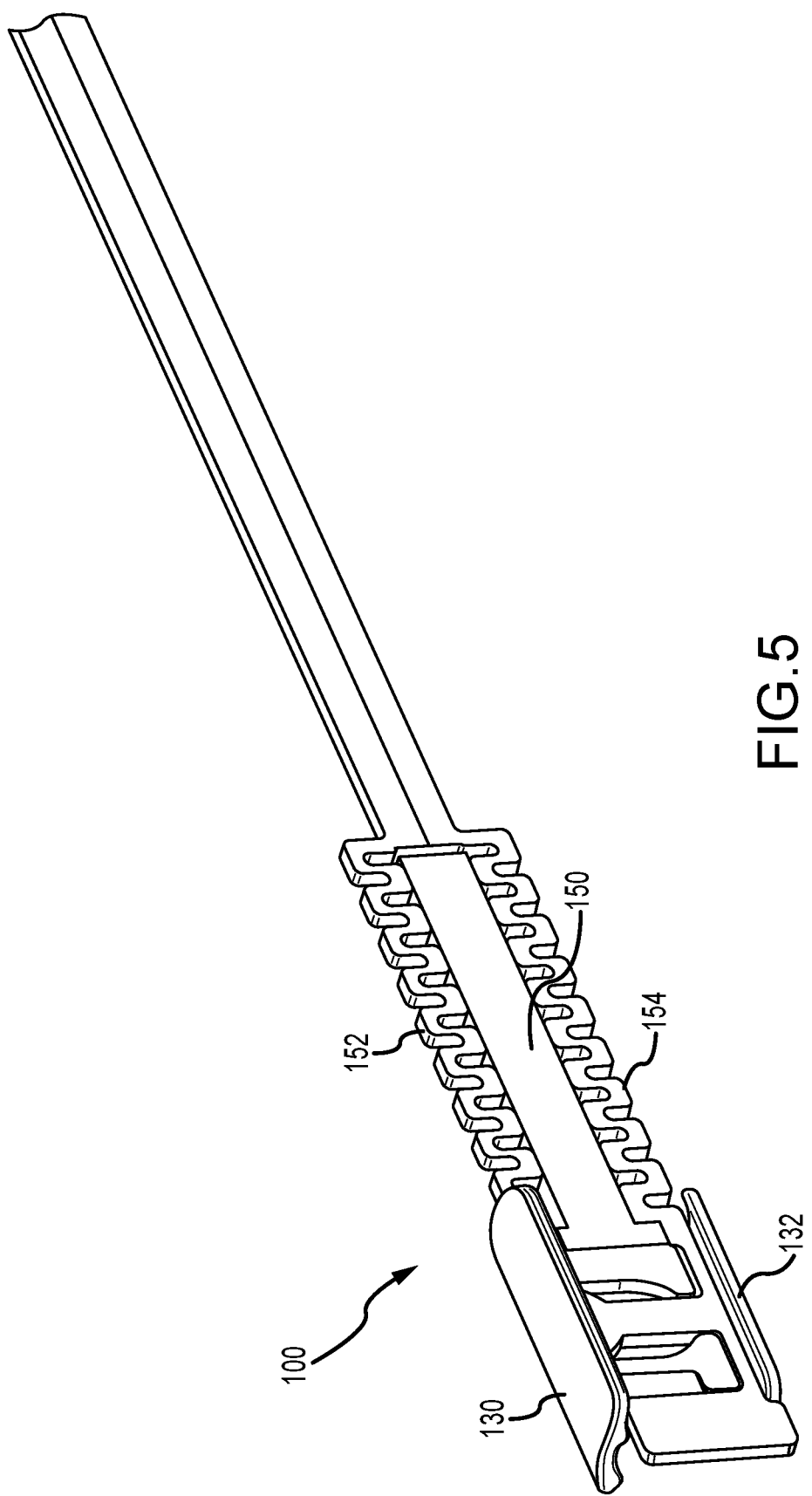
FIG. 5 is a perspective view of the actuator in FIG. 4.
Figure 6:
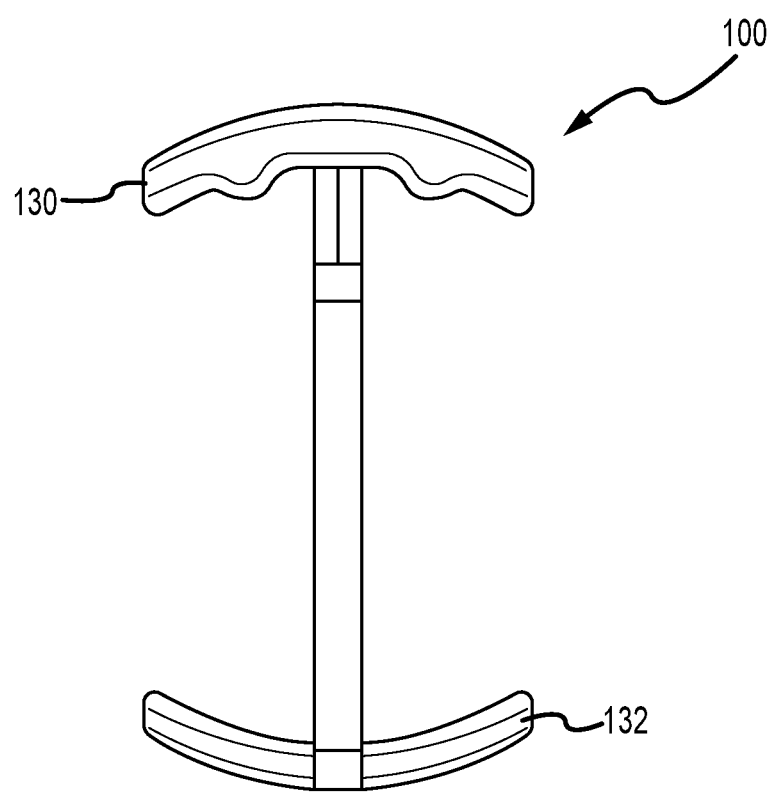
FIG. 6 is an end view of the actuator in FIG. 4.

In some embodiments, and as illustrated in FIGS. 4-6, a clamping mechanism 100 may include a rigidizing portion 150, may be provided between the upper actuator 102 or elongated member and lower actuator 108 or elongated member. In some embodiments, the rigidizing portion 150 may be fastened to or unitary with one or both of the upper member 102 or the lower member 108. In some embodiments, the rigidizing portion 150 may be configured to push against a portion 130, 132 of the I-beam to assist with cutting tissue clamped between the jaws of the instrument 300.

That is, I-beam upper and lower portions 130, 132 may be configured to flex open, and thereby do not require a relatively stiff push mechanism, while a relatively stiff central rigidizing portion 150 may push against that portion of the expanding I-beam that includes the cutting mechanism 120. In the embodiment illustrated in FIG. 4, the cutting mechanism 120 is affixed to the upper I-beam portion 130, although those skilled in the art will recognize that the reverse may be equally effective.

Continuing with FIGS. 4-6, in some embodiments, an upper I-beam portion 130 and a lower I-beam portion 132 may be coupled to highly flexible elongated members 152, 154 and a rigidizing portion 150 may be positioned between the highly flexible elongated members 152, 154. That is, the rigidizing portion 150 may be more rigid than are the elongated members 152, 154.

Figure 7:
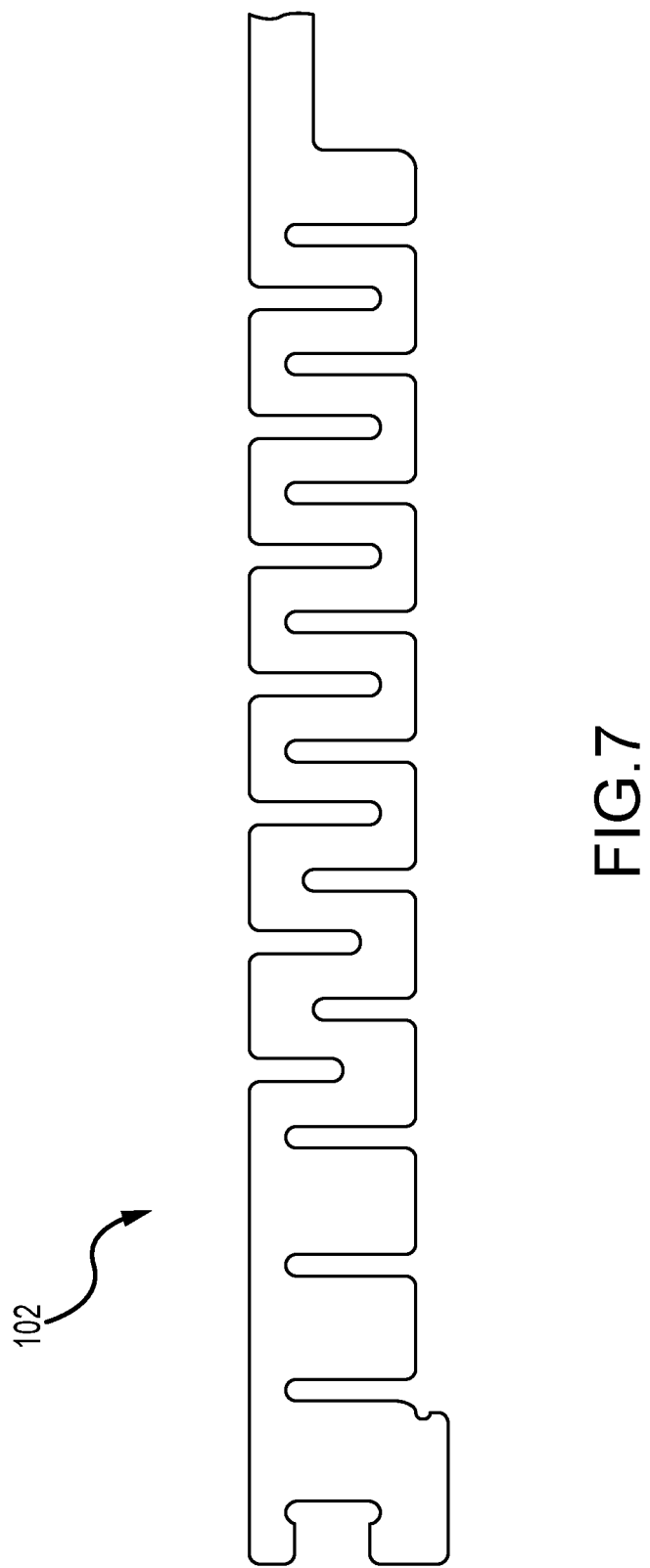
FIG. 7 is a side view of an actuator with cuts removed at a distal end.
Figure 8:
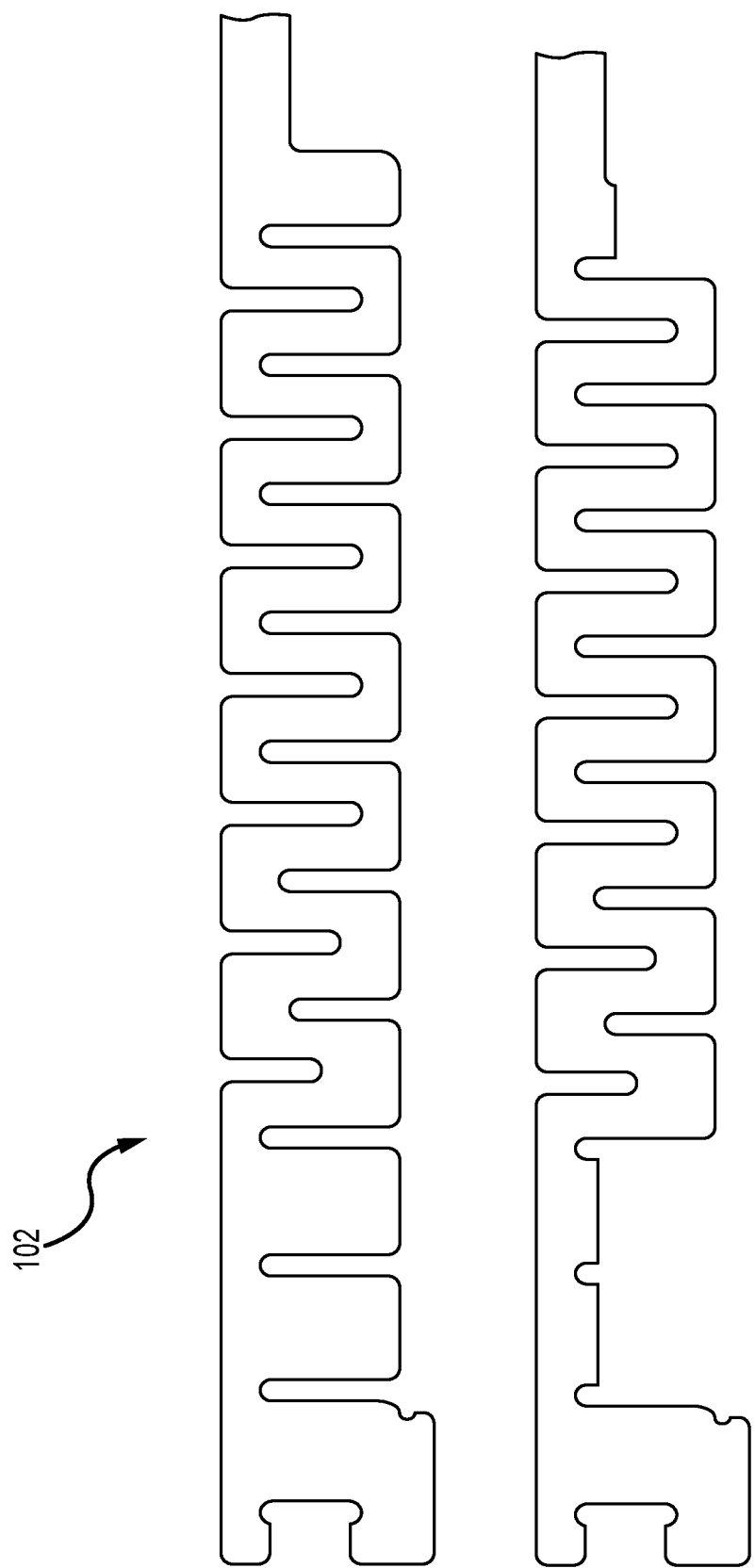
FIG. 8 is a side view illustrating behavior of actuator embodiments.

As illustrated in FIGS. 7-8, in some embodiments, upper and lower elongated members 102, 108 may include sections with material removed to inhibit recovery instead of stiffening the design. The same amount of movement may occur, but the part may permanently deform at the indicated weak spots.

The forces bending the clamping mechanism 100 may "find" weak areas and "ignore" strong areas.

In bend, the two versions in FIG. 8 may behave nearly identically.

Figure 9:
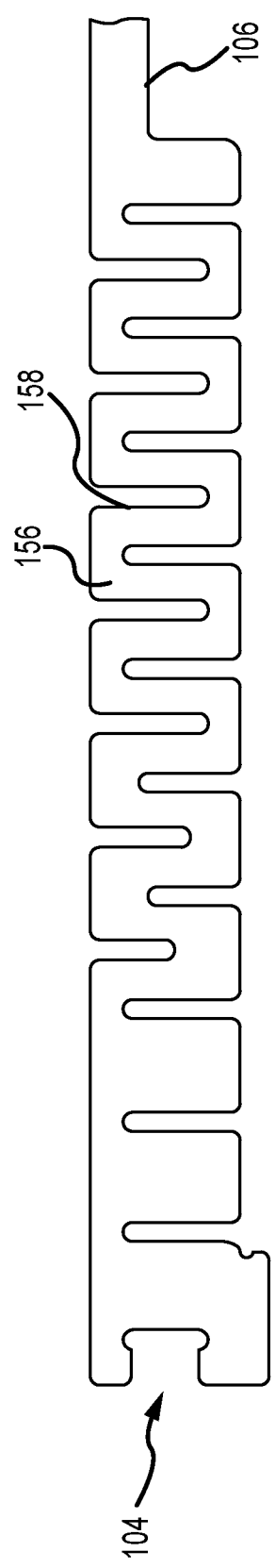
FIG. 9 is a side view illustrating behavior of actuator embodiments.

Turning now to FIG. 9, the clamping mechanism 100, such as with a spring-type design, may have a consistent cross-sectional area across a plurality of legs 156, 158 while maintaining full beam height (A=B). During flex, all areas of the spring experience equal stress.

Figure 10:
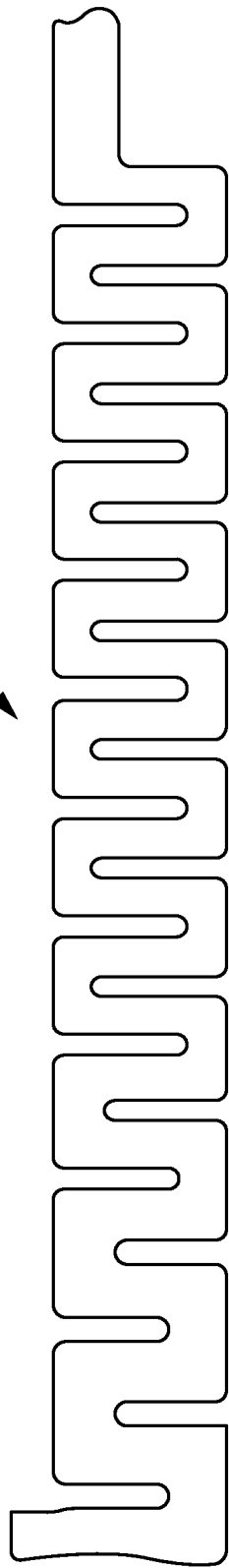
FIG. 10 is a side view illustrating behavior of actuator embodiments.

Referring to FIG. 10, in some embodiments, one may increase both A and B toward distal end to stiffen design this distal portion of the upper and/or lower member 102, 108.

Figure 11:
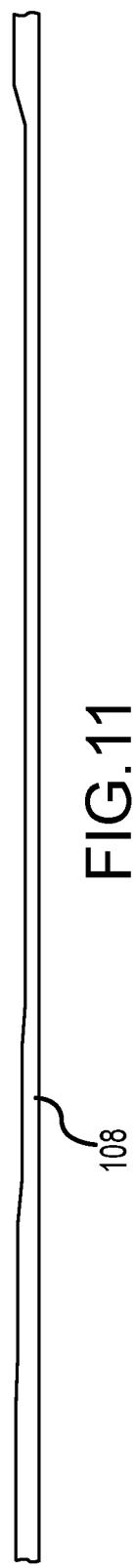
FIG. 11 is a side view illustrating behavior of actuator embodiments.

Referring to FIG. 11, in some embodiments, the flex portion 122 may pack more flexibility in a shorter length. These two designs should have similar flexibility from tip to tip, but the straight design flexes over a much longer length.

Figure 12:
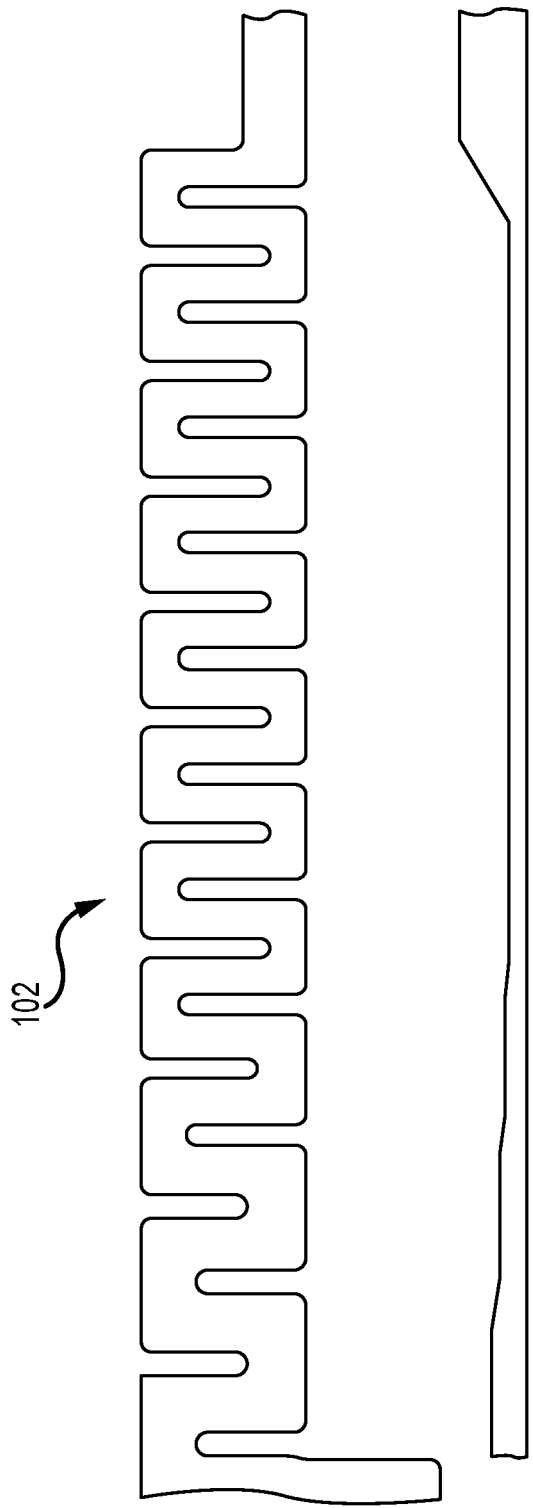
FIG. 12 is a side view illustrating behavior of actuator embodiments.
Figure 13:
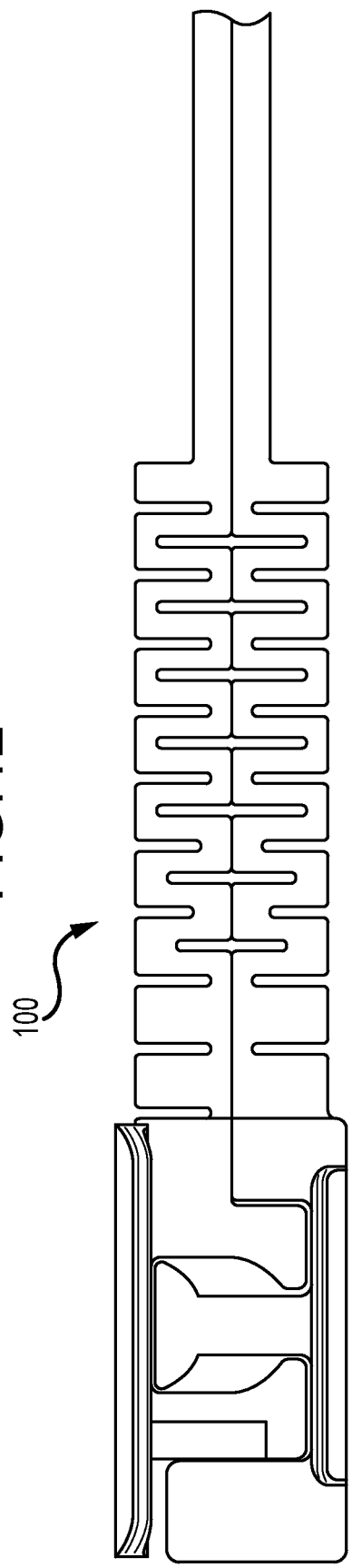
FIG. 13 is a side view of an actuator according to some embodiments.
Figure 14:
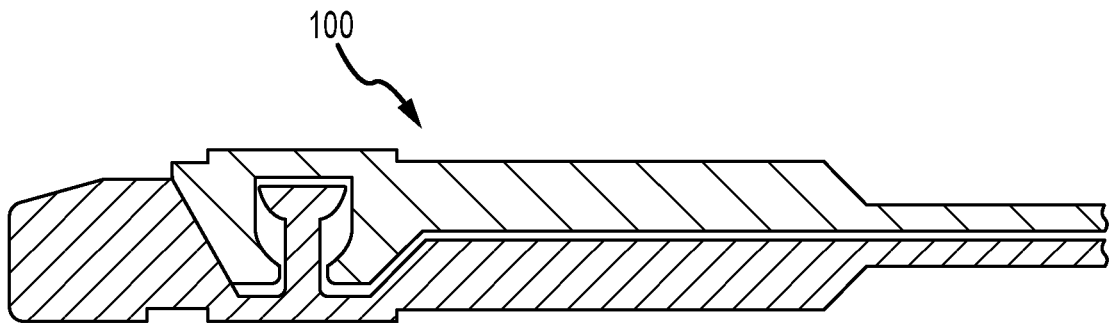
FIG. 14 is a side view of an actuator according to some embodiments.
Figure 15:
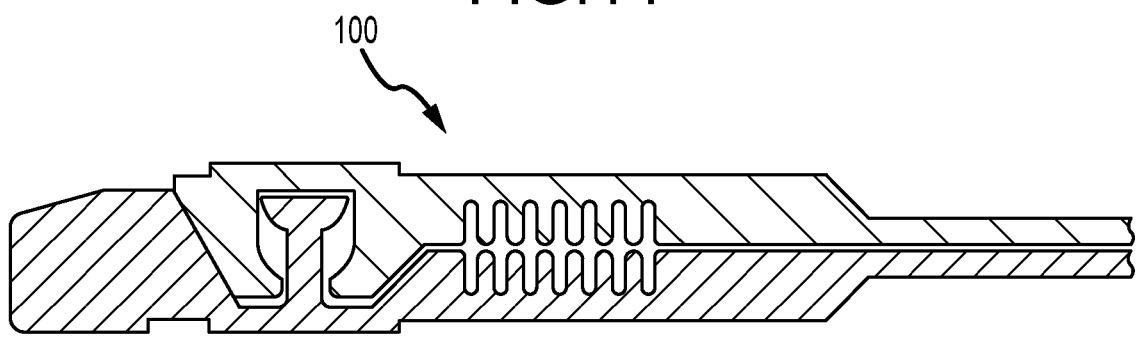
FIG. 15 is a side view of an actuator according to some embodiments.
Figure 16:
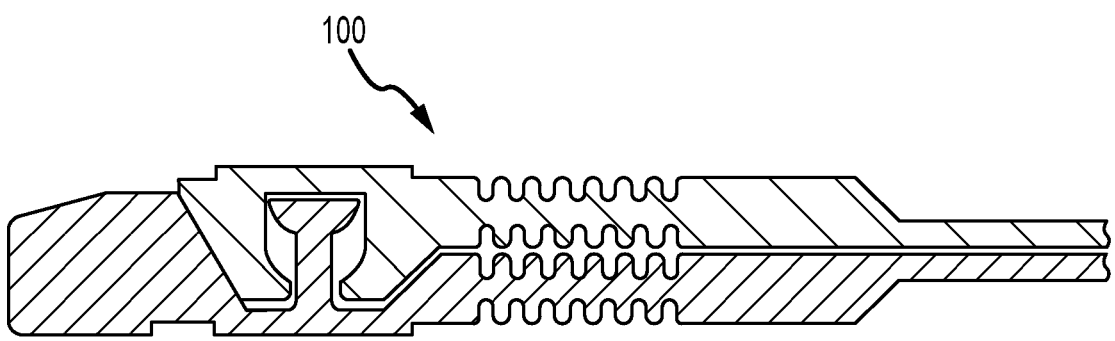
FIG. 16 is a side view of an actuator according to some embodiments.
Figure 17:
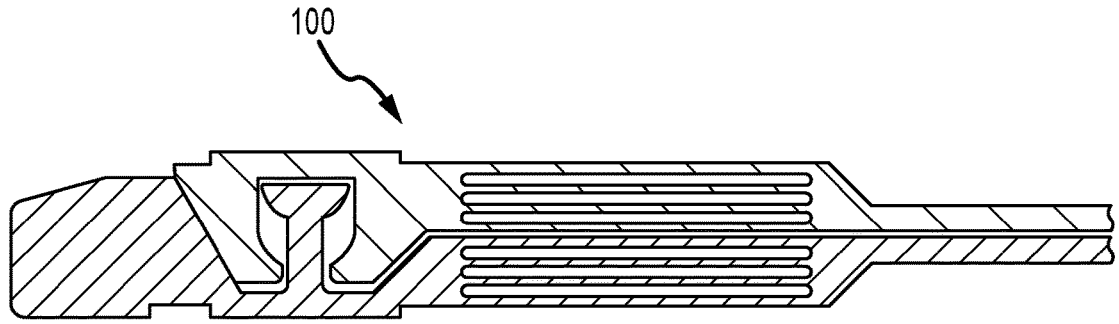
FIG. 17 is a side view of an actuator according to some embodiments.
Figure 18:
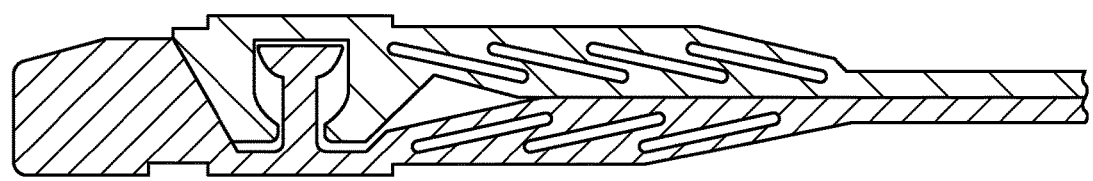
FIG. 18 is a side view of an actuator according to some embodiments.
Figure 19:
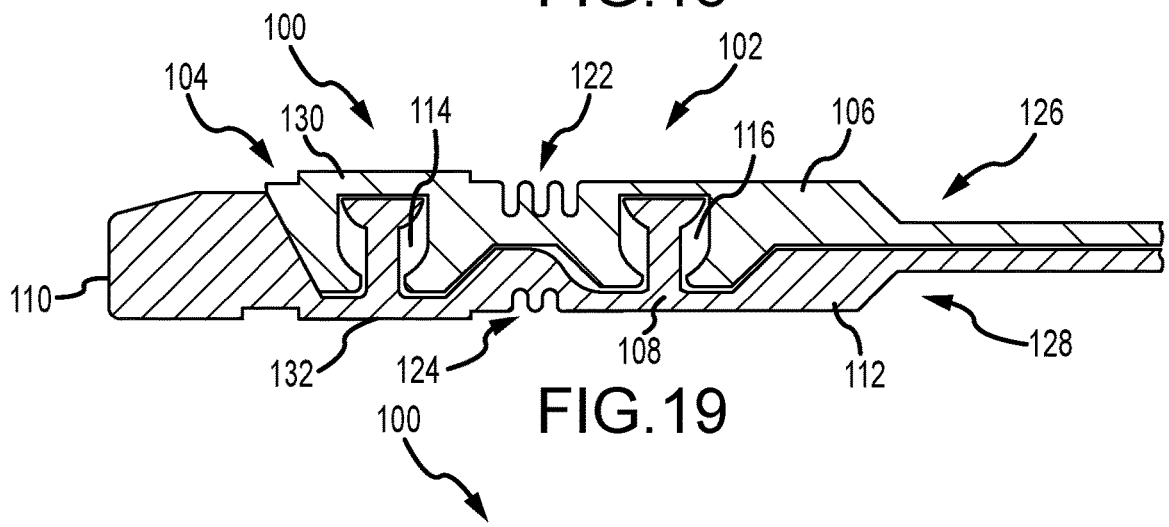
FIG. 19 is a side view of an actuator according to some embodiments.
Figure 20:
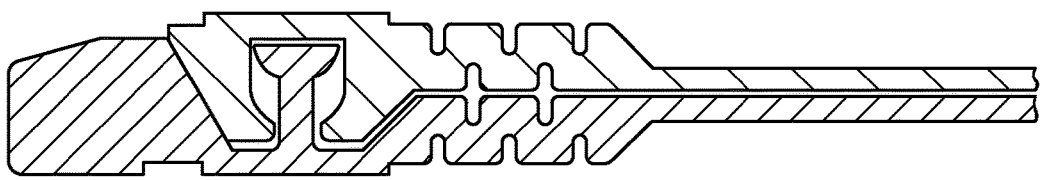
FIG. 20 is a side view of an actuator according to some embodiments.
Figure 21:
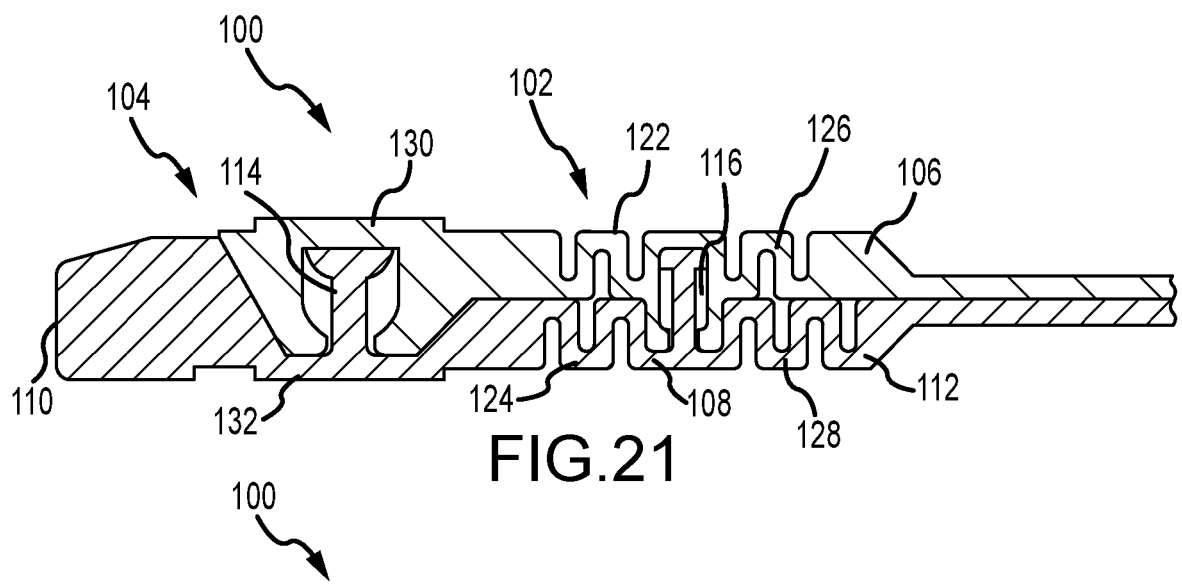
FIG. 21 is a side view of an actuator according to some embodiments.
Figure 22:
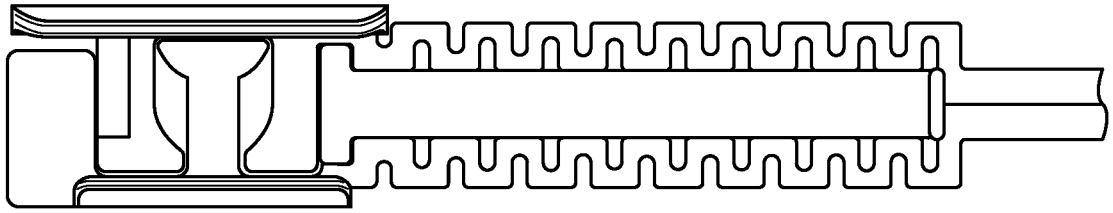
FIG. 22 is a side view of an actuator according to some embodiments.

Referring to FIG. 12, in order to get the same amount of flex in the same length with a straight design, the material needs to be much thinner and weaker in the flex section, making is susceptible to permanent deformation.

FIGS. 13-22 illustrate a variety of clamping mechanism 100 embodiments.

FIGS. 23-32 illustrate a variety of clamping mechanisms 100, a surgical stapler suitable for use therewith, and a method of use.

Figure 23:
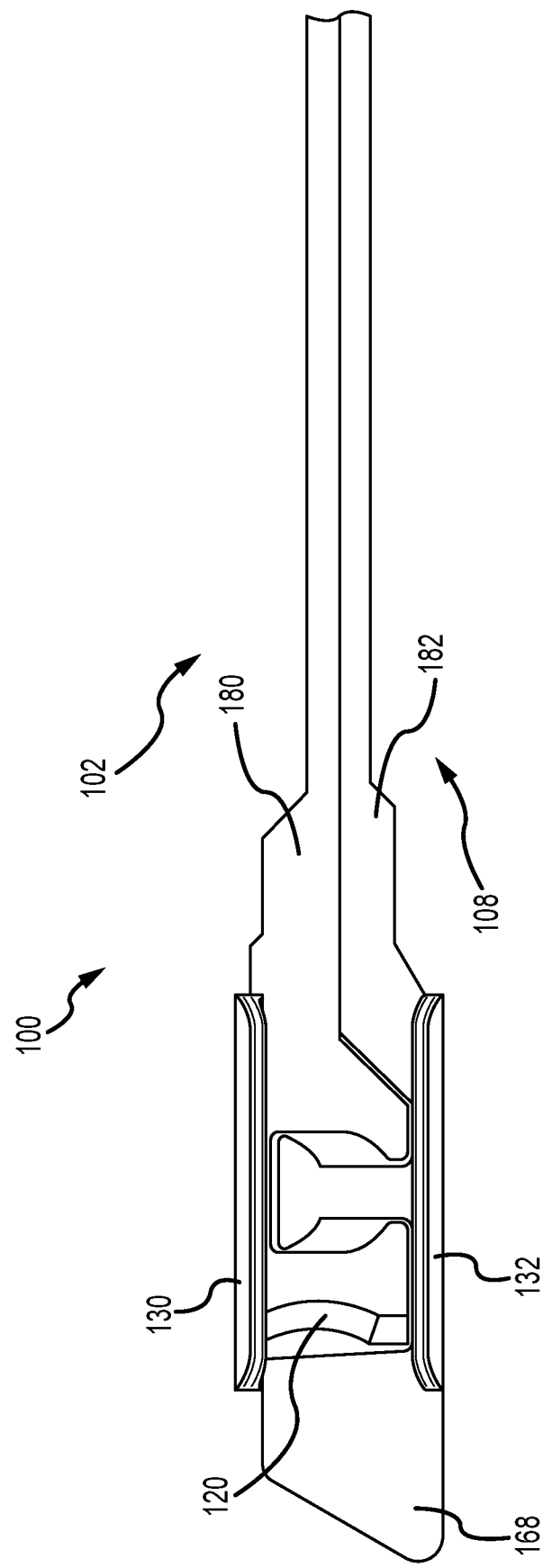
FIG. 23 is a side view of a clamping mechanism according to some embodiments.
Figure 24:
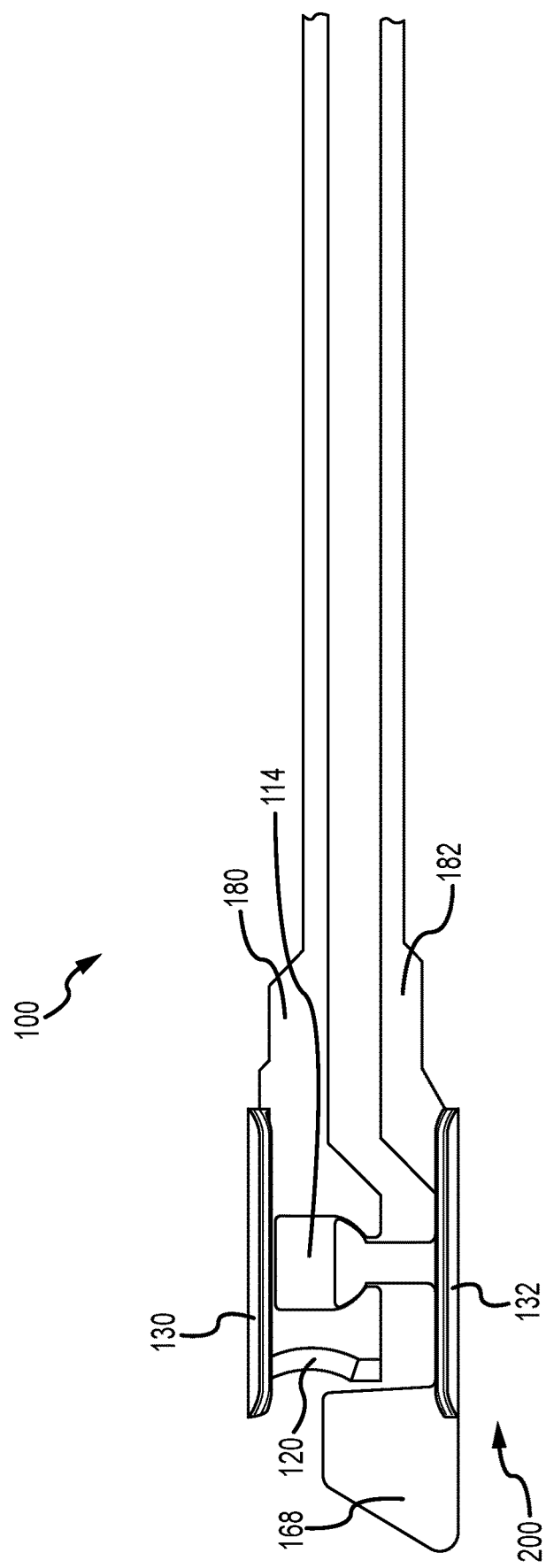
FIG. 24 is a side view of the mechanism in FIG. 23 in an expanded configuration.
Figure 25:
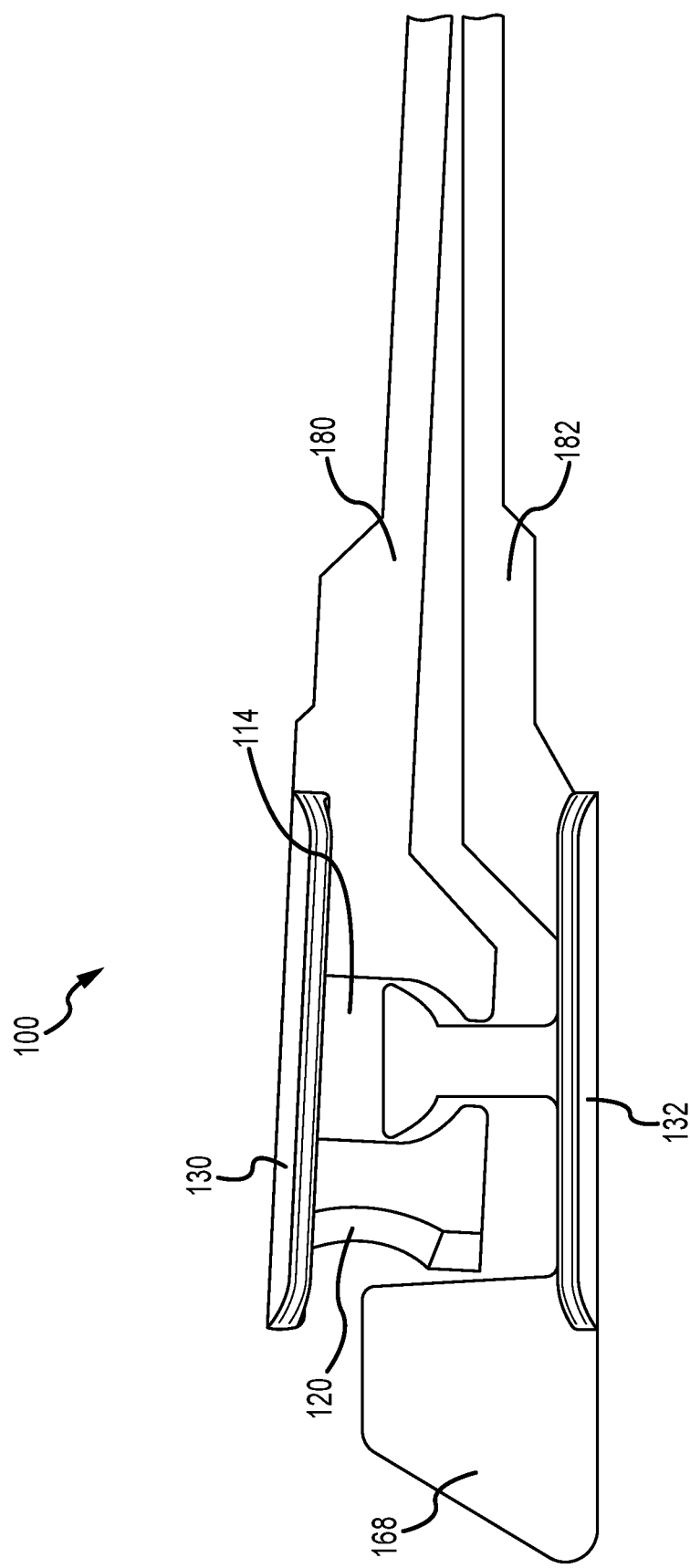
FIG. 25 is a side view of the mechanism in FIG. 23 in a partially-expanded configuration.

With specific reference to FIG. 23, the clamping mechanism 100 may have an upper elongated member 102 and a lower elongated member 108.

In some embodiments, the upper elongated member 102 may be unitary with or coupled to a cutting mechanism 120 and an upper I-beam portion 130 and the lower elongated member 108 may be coupled to or unitary with a lower I-beam portion 132. Stiffening regions 180, 182 may be positioned between the I-beam portions 130, 132 and the proximal ends of the elongated members 102, 108. The stiffening regions 180, 182 may be sections of material that are thicker in the vertical direction but not in the horizontal or transverse direction (see e.g. FIG. 2 illustrating the region is not thickened in the horizontal direction) so as to provide a stiffened section that is less prone to bend when a pushing force is applied. That is, the proximal portion of the elongated members 102, 108 may be more flexible than at the stiffening regions 180, 182.

As illustrated in FIGS. 1, 2, 3, 19, 21, 28, 29, and 30, in some embodiments, a clamping mechanism 100 for a surgical instrument (not illustrated) may be provided. The clamping mechanism 100 may have an upper elongated member 102 having a distal portion 104 and a proximal portion 106. The clamping mechanism 100 may have a lower elongated member 108 having a distal portion 110 and a proximal portion 112.

The upper and lower elongated members 102, 108 may be configured to engage each other at a first interlock 114 and a second interlock 116. The first interlock 114 may be positioned distal of the second interlock 116. The clamping mechanism 100 may be movable between a first configuration, a second configuration, and a third configuration.

Figure 28:
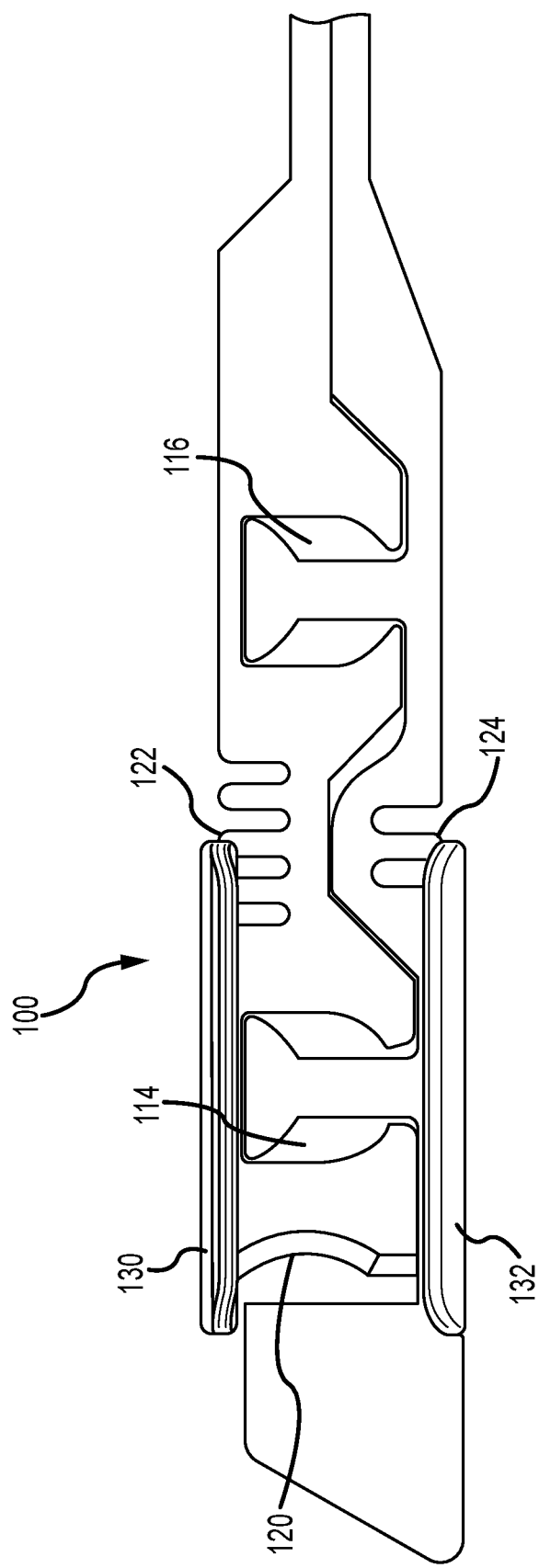
FIG. 28 is a side view of a clamping mechanism suitable for use in the surgical stapler of FIG. 26.

As illustrated in FIG. 28, in the first configuration, the upper and lower elongated members 102, 108 are approximated towards each other and the first and second interlocks 114, 116 are not engaged.

Figure 29:
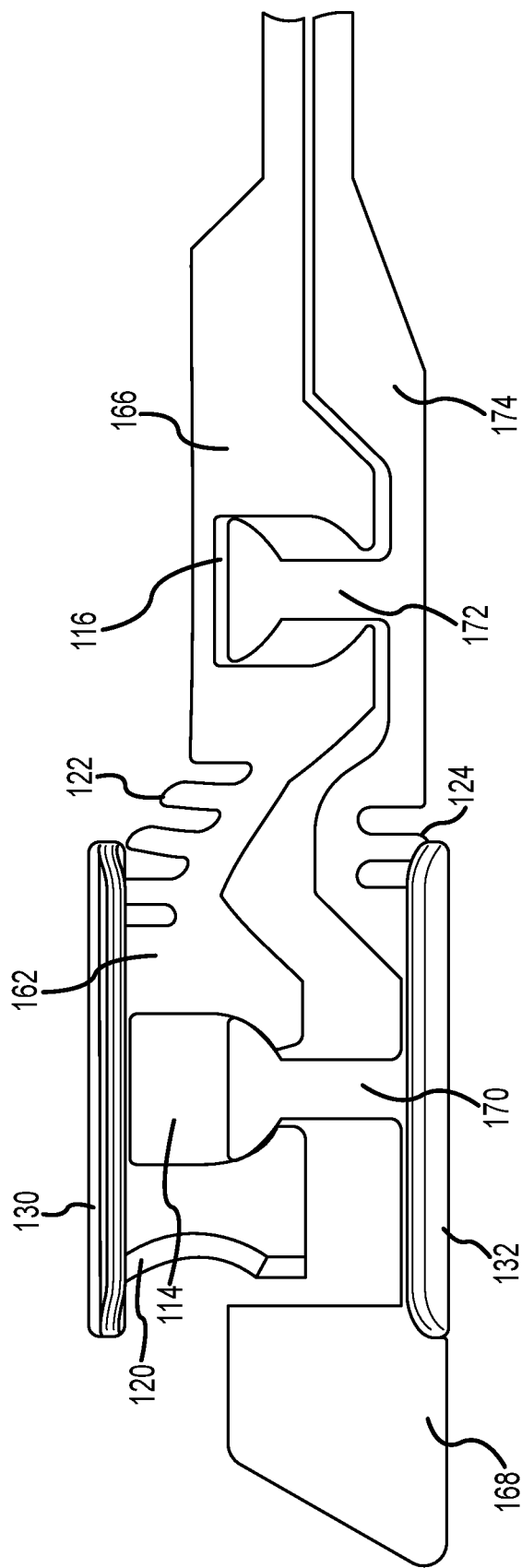
FIG. 29 is a side view of the mechanism in FIG. 28 in a partially-expanded state.

As illustrated in FIG. 29, in the second configuration, the distal portion 104, 110 of the upper and lower elongated members 102, 108 are moved away from each other, the first interlock 114 is engaged, and the second interlock 116 is not engaged.

Figure 30:
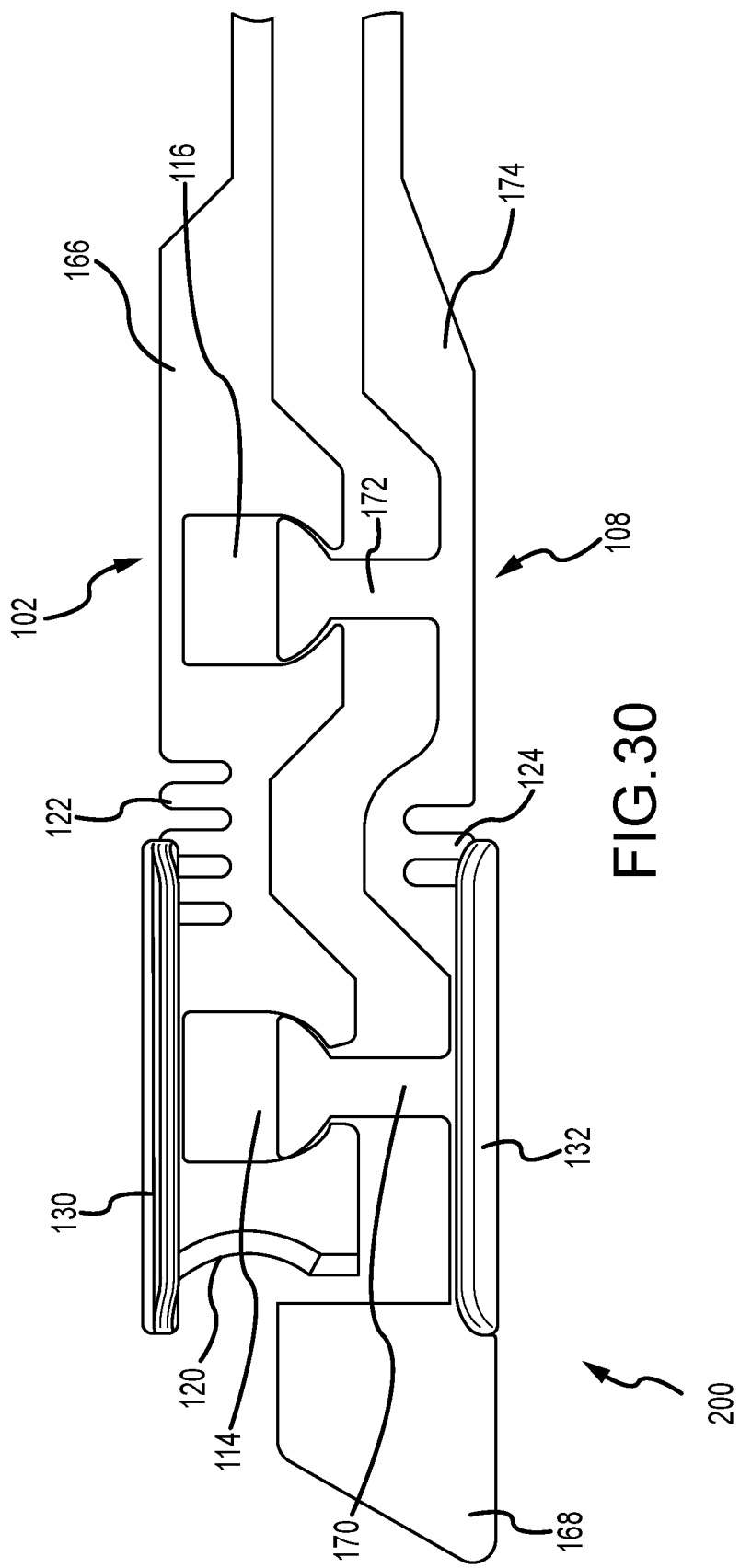
FIG. 30 is a side view of the mechanism in FIG. 28 in a fully expanded state.
Figure 31:
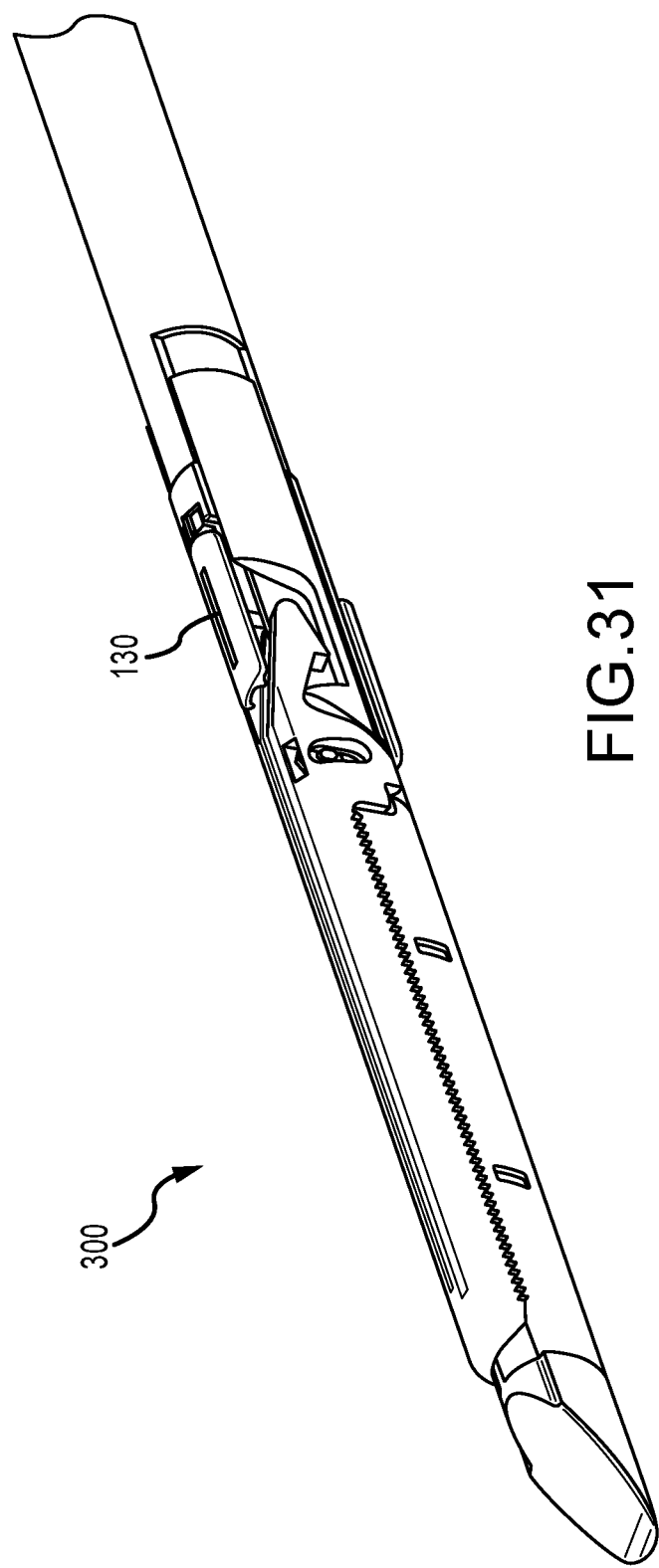
FIG. 31 is a perspective view of a surgical stapler with the mechanism in FIG. 28.

As illustrated in FIG. 30, in the third configuration, the distal portions 104, 110 of the upper and lower elongated members 102, 108 are moved away from each other relatively, the proximal portions 106, 112 of the upper and lower elongated members 102, 108 are moved away from each other relatively, the first interlock 114 is engaged, and the second interlock 116 is engaged.

In some embodiments, the distal portion 104, 110 of one of the upper elongated member 102 or the lower elongated member 108 comprises a cutting mechanism 120. The cutting mechanism 120 may be a knife edge positioned at the distal portion 104, 110.

In some embodiments, each of the first interlock 114 and the second interlock 116 has a flange engagement between the upper and lower elongated members 102, 108 to limit expansion of the upper and lower elongated members 102, 108 to a predetermined distance.

The upper elongated member 102 may have a first flex region 122 between the first interlock 114 and the second interlock 116, the first flex region 122 configured to bend to allow the distal portion 104 of the upper elongated member 102 to rotate relative to the proximal portion 106 of the upper elongated member 102.

In some embodiments, the lower elongated member 108 has a second flex region 124 between the first interlock 114 and the second interlock 116, the second flex region 124 configured to bend to allow the distal portion 110 of the lower elongated member 108 to rotate relative to the proximal portion 112 of the lower elongated member 108.

The upper elongated member 102 may have a flex region 126 positioned proximal of both the first interlock 114 and the second interlock 116, the flex region 126 configured to bend to allow the distal portion 104 of the upper elongated member 102 to rotate relative to the proximal portion 106 of the upper elongated member 102.

In some embodiments, the lower elongated member 108 has a flex region 128 proximal of both the first interlock 114 and the second interlock 116, the flex region 128 configured to bend to allow the distal portion 110 of the lower elongated member 108 to rotate relative to the proximal portion 112 of the lower elongated member 108.

In some embodiments, the first flex region 122 is configured to allow more deflection than does the second flex region 124. In some embodiments, the flex region 126 allows a different amount of deflection than does the flex region 128.

In some embodiments, the upper elongated member 102 has a first I-beam portion 130 configured to engage one of an anvil or an upper jaw (not illustrated) of the surgical instrument. The lower elongated member 108 may have a second I-beam portion 132 configured to engage one of a staple housing or a lower jaw (not illustrated) of the surgical instrument. See also FIG. 31.

Figure 32:
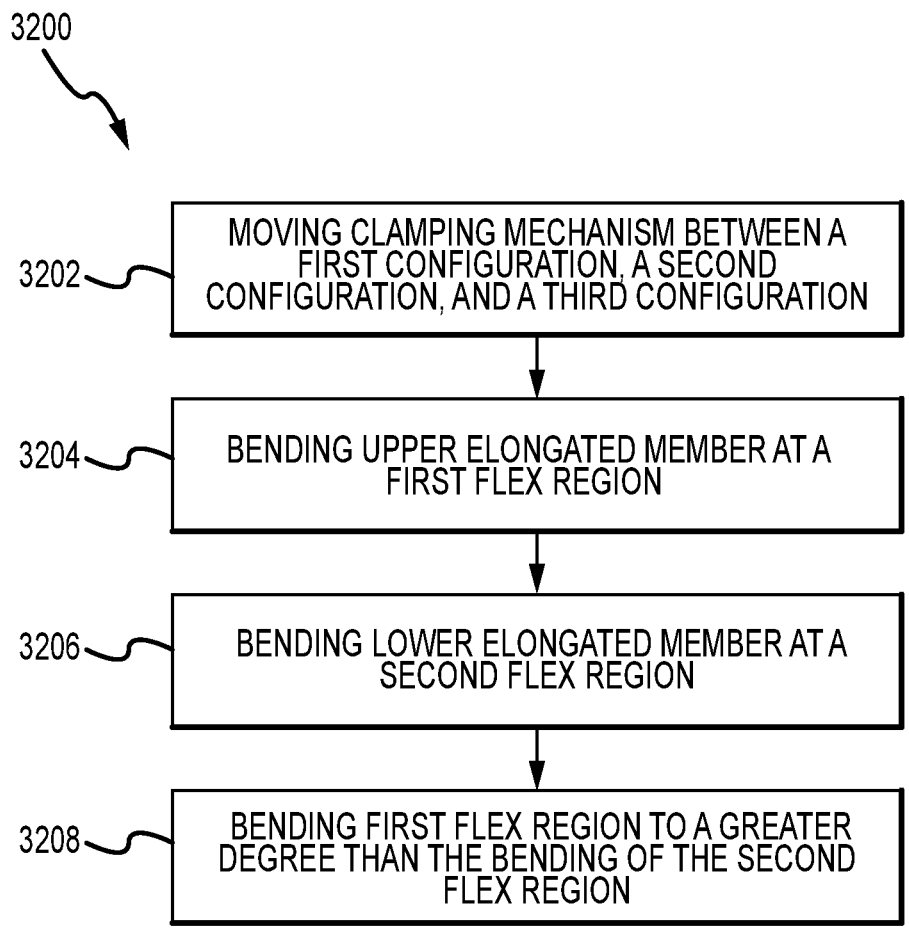
FIG. 32 is a flowchart of a method.

Turning now to FIG. 32, a method 3200 of using a surgical instrument is described. The surgical instrument may be substantially as previously described herein. The instrument may have a clamping mechanism as previously described herein. The method 3200 may include 3202 moving the clamping mechanism between a first configuration, a second configuration, and a third configuration. In the first configuration, the upper and lower elongated members are approximated towards each other and the first and second interlocks are not engaged. In the second configuration, the distal portion of the upper and lower elongated members are moved away from each other, the first interlock is engaged, and the second interlock is not engaged. In the third configuration, the distal portions of the upper and lower elongated members are moved away from each other relatively, the proximal portions of the upper and lower elongated members are moved away from each other relatively, the first interlock is engaged, and the second interlock is engaged.

The method 3200 may also include bending 3204 the upper elongated member at a first flex region, the first flex region positioned between the first interlock and the second interlock.

The method 3200 may also include bending 3206 the lower elongated member at a second flex region, the second flex region positioned between the first interlock and the second interlock.

The method 3200 may also include bending 3208 the first flex region to a greater degree than the bending of the second flex region.

The previous description of the disclosed embodiments and examples is provided to enable any person skilled in the art to make or use the present invention as defined by the claims. Thus, the present disclosure is not intended to be limited to the examples disclosed herein. Various modifications to these embodiments may be readily apparent to those skilled in the art, and the generic principles defined herein may be applied to other embodiments without departing from the scope of the invention as claimed.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "fastener" should be understood to encompass disclosure of the act of "fastening"—whether explicitly discussed or not—and, conversely, were there only disclosure of the act of "fastening", such a disclosure should be understood to encompass disclosure of a "fastening mechanism". Such changes and alternative terms are to be understood to be explicitly included in the description.

Moreover, the claims shall be construed such that a claim that recites "at least one of A, B, or C" shall read on a device that requires "A" only. The claim shall also read on a device that requires "B" only. The claim shall also read on a device that requires "C" only.

Similarly, the claim shall also read on a device that requires "A+B". The claim shall also read on a device that requires "A+B+C", and so forth.

The claims shall also be construed such that any relational language (e.g. perpendicular, straight, parallel, flat, etc.) is understood to include the recitation "within a reasonable manufacturing tolerance at the time the device is manufactured or at the time of the invention, whichever manufacturing tolerance is greater".

Those skilled in the art can readily recognize that numerous variations and substitutions may be made in the invention, its use and its configuration to achieve substantially the same results as achieved by the embodiments described herein.

Accordingly, there is no intention to limit the invention to the disclosed exemplary forms. Many variations, modifications and alternative constructions fall within the scope and spirit of the invention as expressed in the claims.

What is claimed is:

1. A clamping mechanism for a surgical instrument, comprising:
   an upper elongated member having a distal portion and a proximal portion; and
   a lower elongated member having a distal portion and a proximal portion; wherein
   the upper and lower elongated members are configured to engage each other at a first interlock and a second interlock, the first interlock distal of the second interlock, whereby the clamping mechanism is movable between a first configuration, a second configuration, and a third configuration,
   wherein, in the first configuration, the upper and lower elongated members are approximated towards each other and the first and second interlocks are not engaged,
   wherein, in the second configuration, the distal portion of the upper and lower elongated members are moved away from each other, the first interlock is engaged, and the second interlock is not engaged,
   wherein, in the third configuration, the distal portions of the upper and lower elongated members are moved away from each other relatively, the proximal portions of the upper and lower elongated members are moved away from each other relatively, the first interlock is engaged, and the second interlock is engaged,
   and wherein the surgical instrument is a surgical stapler.

2. The clamping mechanism of claim 1, wherein:
   the distal portion of one of the upper elongated member or the lower elongated member comprises a cutting mechanism.

3. The clamping mechanism of claim 1, wherein:
   each of the first interlock and the second interlock comprises a flange engagement between the upper and lower elongated members to limit expansion of the upper and lower elongated members to a predetermined distance.

4. The clamping mechanism of claim 1, wherein:
   the upper elongated member comprises a first flex region between the first interlock and the second interlock, the first flex region configured to bend to allow the distal portion of the upper elongated member to rotate relative to the proximal portion of the upper elongated member.

5. The clamping mechanism of claim 4, wherein:
   the lower elongated member comprises a second flex region between the first interlock and the second interlock, the second flex region configured to bend to allow the distal portion of the lower elongated member to rotate relative to the proximal portion of the lower elongated member.

6. The clamping mechanism of claim 5, wherein:
   the first flex region is configured to allow more deflection than does the second flex region.

7. The clamping mechanism of claim 1, wherein:
   the upper elongated member comprises a first I-beam portion configured to engage one of an anvil or an upper jaw of the surgical instrument; and
   the lower elongated member comprises a second I-beam portion configured to engage one of a staple housing or a lower jaw of the surgical instrument.

8. A surgical instrument, comprising:
   a clamping mechanism, the clamping mechanism comprising:
   (a) an upper elongated member having a distal portion and a proximal portion; and
   (b) a lower elongated member having a distal portion and a proximal portion; wherein
   the upper and lower elongated members are configured to engage each other at a first interlock and a second interlock, the first interlock distal of the second interlock, whereby the clamping mechanism is movable between a first configuration, a second configuration, and a third configuration,
   wherein, in the first configuration, the upper and lower elongated members are approximated towards each other and the first and second interlocks are not engaged,
   wherein, in the second configuration, the distal portion of the upper and lower elongated members are moved away from each other, the first interlock is engaged, and the second interlock is not engaged,
   wherein, in the third configuration, the distal portions of the upper and lower elongated members are moved away from each other relatively, the proximal portions of the upper and lower elongated members are moved away from each other relatively, the first interlock is engaged, and the second interlock is engaged,
   and wherein the surgical instrument is a surgical stapler.

9. The surgical instrument of claim 8, wherein:
   the distal portion of one of the upper elongated member or the lower elongated member comprises a cutting mechanism.

10. The surgical instrument of claim 8, wherein:
    each of the first interlock and the second interlock comprises a flange engagement between the upper and lower elongated members to limit expansion of the upper and lower elongated members to a predetermined distance.

11. The surgical instrument of claim 8, wherein:
    the upper elongated member comprises a first flex region between the first interlock and the second interlock, the first flex region configured to bend to allow the distal portion of the upper elongated member to rotate relative to the proximal portion of the upper elongated member.

12. The surgical instrument of claim 11, wherein:
    the lower elongated member comprises a second flex region between the first interlock and the second interlock, the second flex region configured to bend to allow the distal portion of the lower elongated member to rotate relative to the proximal portion of the lower elongated member.

13. The surgical instrument of claim 12, wherein:
    the first flex region is configured to allow more deflection than does the second flex region.

14. The surgical instrument of claim 8, wherein:
    the surgical instrument comprises one of an anvil or an upper jaw and one of a staple housing or a lower jaw;

the upper elongated member comprises a first I-beam portion configured to engage the one of the anvil or the upper jaw; and the lower elongated member comprises a second I-beam portion configured to engage the one of the staple housing or the lower jaw.

15. A method of using a surgical instrument, the surgical instrument having a clamping mechanism, the clamping mechanism having an upper elongated member with a distal portion and a proximal portion and a lower elongated member with a distal portion and a proximal portion, the upper and lower elongated members configured to engage each other at a first interlock and a second interlock, the first interlock distal of the second interlock, the method comprising:

moving the clamping mechanism between a first configuration, a second configuration, and a third configuration, wherein, in the first configuration, the upper and lower elongated members are approximated towards each other and the first and second interlocks are not engaged, wherein, in the second configuration, the distal portion of the upper and lower elongated members are moved away from each other, the first interlock is engaged, and the second interlock is not engaged, wherein, in the third configuration, the distal portions of the upper and lower elongated members are moved away from each other relatively, the proximal portions of the upper and lower elongated members are moved away from each other relatively, the first interlock is engaged, and the second interlock is engaged, and wherein the surgical instrument is a surgical stapler.

16. The method of claim 15, wherein:

the distal portion of one of the upper elongated member or the lower elongated member comprises a cutting mechanism.

17. The method of claim 15, wherein:

each of the first interlock and the second interlock comprises a flange engagement between the upper and lower elongated members to limit expansion of the upper and lower elongated members to a predetermined distance.

18. The method of claim 15, further comprising:

bending the upper elongated member at a first flex region, the first flex region positioned between the first interlock and the second interlock.

19. The method of claim 18, further comprising:

bending the lower elongated member at a second flex region, the second flex region positioned between the first interlock and the second interlock.

20. The method of claim 19, further comprising:

the bending the first flex region comprises bending the first flex region to a greater degree than the bending of the second flex region.

21. The method of claim 15, wherein:

the surgical instrument comprises one of an anvil or an upper jaw and one of a staple housing or a lower jaw;

the upper elongated member comprises a first I-beam portion configured to engage the one of the anvil or the upper jaw; and the lower elongated member comprises a second I-beam portion configured to engage the one of the staple housing or the lower jaw.

* * * * *